United States Patent
Shur et al.

(10) Patent No.: US 7,170,056 B2
(45) Date of Patent: Jan. 30, 2007

(54) METHODOLOGY AND APPARATUS FOR LEAKAGE DETECTION

(75) Inventors: Dmirty Shur, Holon (IL); Alexander Kadyshevitch, Modiin (IL)

(73) Assignee: Applied Materials, Israel, Ltd., Rehovot (IL)

( * ) Notice: Subject to any disclaimer, the term of this patent is extended or adjusted under 35 U.S.C. 154(b) by 6 days.

(21) Appl. No.: 11/025,197

(22) Filed: Dec. 29, 2004

(65) Prior Publication Data

US 2005/0279935 A1 Dec. 22, 2005

Related U.S. Application Data

(60) Provisional application No. 60/581,874, filed on Jun. 21, 2004.

(51) Int. Cl.
*H01J 37/256* (2006.01)
*G01N 23/225* (2006.01)

(52) U.S. Cl. .................. 250/310; 250/307; 324/751

(58) Field of Classification Search ................. 250/310
See application file for complete search history.

(56) References Cited

U.S. PATENT DOCUMENTS 5,097,204 A * 3/1992 Yoshizawa et al. ......... 324/751
5,612,626 A * 3/1997 Golladay ..................... 324/751

FOREIGN PATENT DOCUMENTS

JP 06-326165 * 11/1994

* cited by examiner

*Primary Examiner*—Nikita Wells
*Assistant Examiner*—James J. Leybourne
(74) *Attorney, Agent, or Firm*—Tsrek N. Fahmi (57) ABSTRACT

A method for measuring leakage through a dielectric layer of a semiconductor device on a wafer, including irradiating the dielectric layer with a charged particle beam having a beam current. The irradiation generates a wafer current having a relation to the beam current in a selected range of the beam current. The method further includes determining a boundary value of the beam current at which the relation is not satisfied, and determining a leakage current through the dielectric layer in response to the boundary value.

10 Claims, 6 Drawing Sheets

METHODOLOGY AND APPARATUS FOR LEAKAGE DETECTION

CROSS-REFERENCE TO RELATED APPLICATION

This application claims the benefit of U.S. Provisional Patent Application 60/581,874, filed Jun. 21, 2004, which is incorporated herein by reference.

FIELD OF THE INVENTION

The present invention relates generally to measurement of an electrical property of a component of an integrated circuit, and specifically to measurement of current leakage in the component.

BACKGROUND OF THE INVENTION

In fabrication of semiconductor devices on a wafer, measurements of current leakage of dielectric sections of the device are an important part of the overall process, to check that the sections formed conform to their nominal specifications. Leakage measurements are particularly important for dielectric layers, such as those used in dynamic random access memory (DRAM) capacitors, and those forming the gates of transistors. At present, leakage measurements are typically performed on relatively large test structures having sizes greater than 50 µm×50 µm, the test structures being located at a periphery of a die. The test structures simulate the conditions of the layer or section being tested. Measurements of such test structures require that physical connections be made to the structure, so that currents through the structure can be measured.

A method for measuring properties of wafer components using three non-contact techniques is described in an article titled "Diagnosing Processing Problems through Electrical Charge Characterization" by Horner et al., in the Autumn 1999 edition of *Yield Management Solutions*. The article may be found at www.kla-tencor.com/company/magazine/autumn99.html, and is incorporated herein by reference. To perform a measurement, a corona discharge biases the surface of a wafer being inspected, and a vibrating Kelvin probe monitors the wafer surface potential as a function of the charge. A pulsed light source linked to the Kelvin probe is used to generate a photo-voltage. The authors state that use of the three techniques allows extraction of electrical properties of a system being inspected.

A number of other methods for measuring wafer parameters are known in the art. Some of these methods use an electron beam having a variable energy so as to cover both positive and negative charging domains of the materials irradiated by the beam. The positive charging domain is the range of electron energies in which the total yield of secondary and backscattered electrons from the surface layer is greater than the primary electron beam current, while the negative charging domain is the range in which the total yield is less than the primary beam current. These domains are described, for example, by Yacobi et al., in *Microanalysis of Solids* (Plenum Press, New York, 1994) on pages 38–39.

U.S. Patent Application Publication 2003/0071646 to Neo et al., whose disclosure is incorporated herein by reference, describes a method for evaluating a pn junction. The junction is reverse biased, irradiated with an electron beam, and secondary electrons from the junction are collected. The operation is performed sequentially, and a relaxation time of the junction may be determined from the image formed by the secondary electrons.

U.S. Pat. No. 6,294,918 to Hung, whose disclosure is incorporated herein by reference, describes a method for locating a weak circuit in an integrated circuit (IC). An electron beam scans the surface of the IC to determine a threshold current that causes failure in a circuit of the IC. A functionality tester functions simultaneously with the electron beam, and is used to locate weak circuits having insufficient driving currents.

U.S. Pat. No. 6,504,393 to Lo et al., whose disclosure is incorporated herein by reference, describes apparatus for testing a semiconductor structure. The apparatus includes a system, which may be an electron beam, for charging the structure, and an electric field generator which applies a field perpendicular to the surface of the structure to determine the potential of the charge. The charged structure is interrogated with a charged particle beam, such as the electron beam. A secondary electron detector in the apparatus is used to determine voltage contrast data for the structure.

U.S. Pat. No. 6,700,122 to Matsui et al., whose disclosure is incorporated herein by reference, describes a technique for detecting defects in a wafer. An electron beam scans the wafer while the wafer is being moved, and secondary electrons generate an image of the wafer surface. The image may be analyzed to find both the type and the position of defects.

U.S. Pat. No. 6,753,194 to Ushiki et al., whose disclosure is incorporated herein by reference, describes irradiating a region of a semiconductor wafer with an electron beam in order to determine contaminants of the region. A current flowing from the region is measured, and a degree of contamination of the region is determined in response to the current.

An article titled "Reliability limits for the gate insulator in CMOS technology" by Stathis, in the *IBM Journal of Research and Development* 46, Numbers 2/3, 2002, is incorporated herein by reference. The article describes properties of gates of transistors; inter alia, the article states that for a $SiO_2$ gate thickness of ~1.5 nm, a current density greater than about 10 $A/cm^2$ is viewed as leakage.

SUMMARY OF THE INVENTION

In an embodiment of the present invention, a leakage current through a dielectric layer on a wafer is determined by irradiating the layer with a primary charged particle beam, typically an electron beam, having a primary beam current. In a selected range of the beam current, the irradiation generates a wafer current having a relation to the beam current. At a boundary value of the beam current the relation no longer holds, and a leakage current through the layer is determined in response to the boundary value.

At low beam currents the wafer current from the wafer has a direct relation to the beam current, as a function of the secondary electron yield. At higher beam currents, above the boundary value, the wafer current approaches a saturation value. The dielectric layer leakage current is equal to the saturation value of the wafer current.

The irradiating primary beam is operated in a positive charging domain, and an operating value for the beam current is set to ensure that the irradiated feature saturates. The value of the wafer saturation current gives the dielectric layer leakage current.

In a disclosed embodiment, a boundary dielectric layer leakage current density is determined by finding a current vs.

voltage relation for a test structure on the wafer. The test structure has a similar construction to that of a feature on the wafer that is being evaluated. The boundary leakage current density is used to specify nominal leakage currents for features that have a similar construction to that of the test structure.

In one embodiment of the invention, an electrode is positioned above the wafer, and the electrode is biased positively or negatively so as to set a surface voltage of the wafer to be a desired value. The electrode may be used to determine the current vs. voltage relation for the test structure, as well as to enable dielectric layer leakage currents to be measured at different gate voltages. In a disclosed embodiment, the surface voltage is measured by spectrally analyzing energies of electrons generated by the charged beam irradiation of the wafer.

The present invention will be more fully understood from the following detailed description of the embodiments thereof, taken together with the drawings, a brief description of which follows.

DETAILED DESCRIPTION OF EMBODIMENTS

Figure 1:
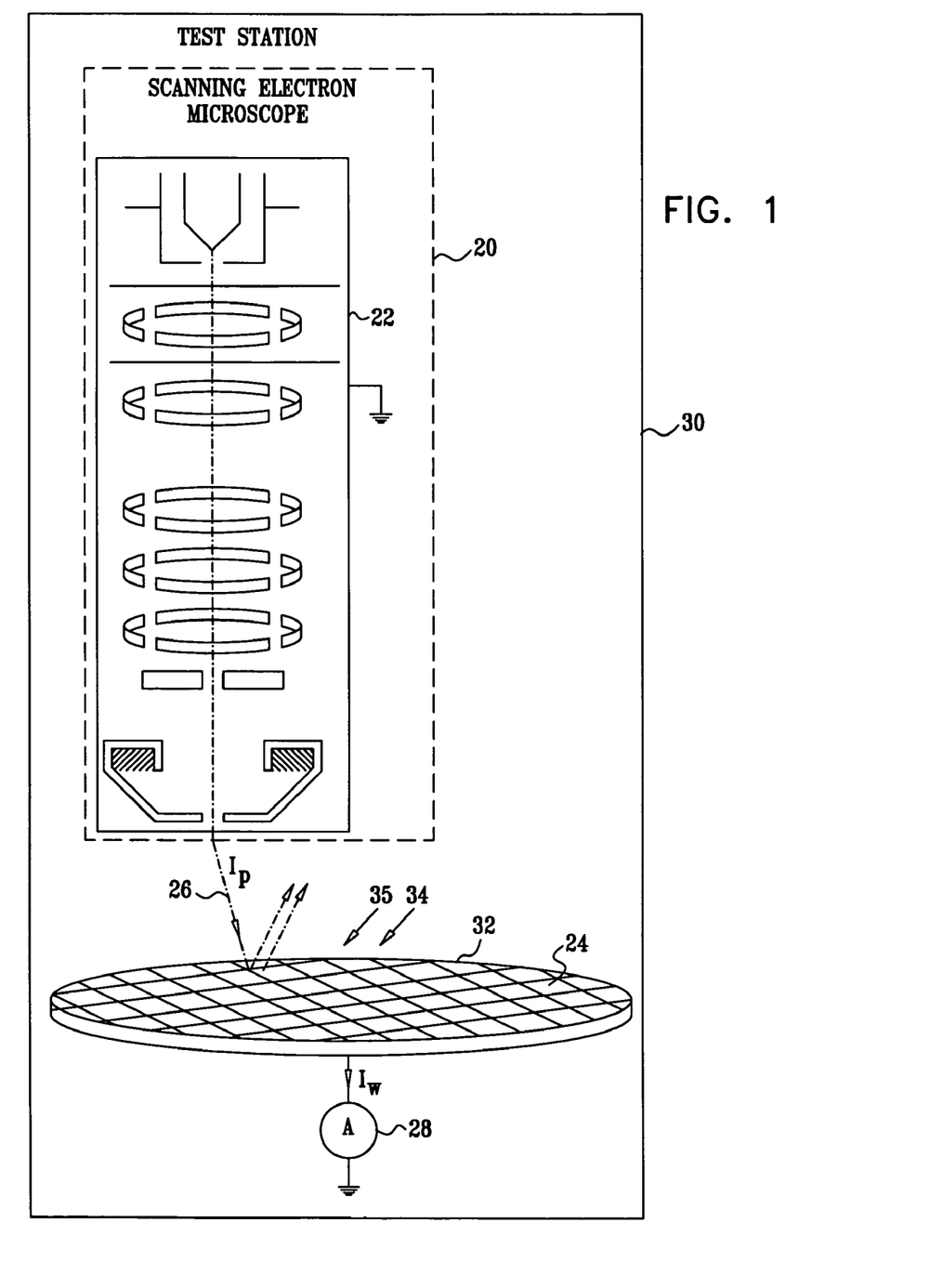
FIG. 1 is a schematic illustration of a gate leakage measurement apparatus, according to an embodiment of the present invention.

Reference is now made to FIG. 1, which is a schematic illustration of a gate leakage measurement apparatus 20, according to an embodiment of the present invention. Apparatus 20 includes a charged particle generator 22 which irradiates a semiconductor wafer 24 with a primary charged particle beam 26. Apparatus 20 is hereinbelow, by way of example, assumed to be a scanning electron microscope (SEM), and beam 26 is assumed to be an electron beam delivering a primary beam current $I_p$ to the wafer. A wafer current $I_w$ flows between the wafer and ground, and is measured by an ammeter 28. Apparatus 20, wafer 24, and ammeter 28 are typically part of a test station 30, a more detailed description of which, together with a description of other components of apparatus 20, is given below with respect to FIG. 3.

A number of generally similar dies 32 are formed on wafer 24, by applying different fabrication stages to the wafer, as is known in the fabrication art, each stage comprising a process such as thin film deposition, patterning, material removal, or doping. Each die 32 includes transistors 34 and/or capacitors 35. By way of example, wafer 24 is assumed to be formed from silicon, and transistors 34 and capacitors 35 are assumed to be formed by the stages referred to above using complementary metal oxide semiconductor (CMOS) technology. It will be appreciated, however, that the principles of the present invention are not limited to a specific type of wafer, nor to a specific technology used to form transistors and/or capacitors and/or any other dielectric comprising element on the wafer, nor to a specific type of component formed on the wafer. By way of example, except where otherwise stated, the following description is directed to measurements of leakage of gates of a transistor. Those skilled in the art will be able to adapt the description, mutatis mutandis, to cover leakage through other structures comprising dielectric layers, such as those of capacitors, and all such structures are assumed to be comprised within the scope of the present invention.

Figure 2:
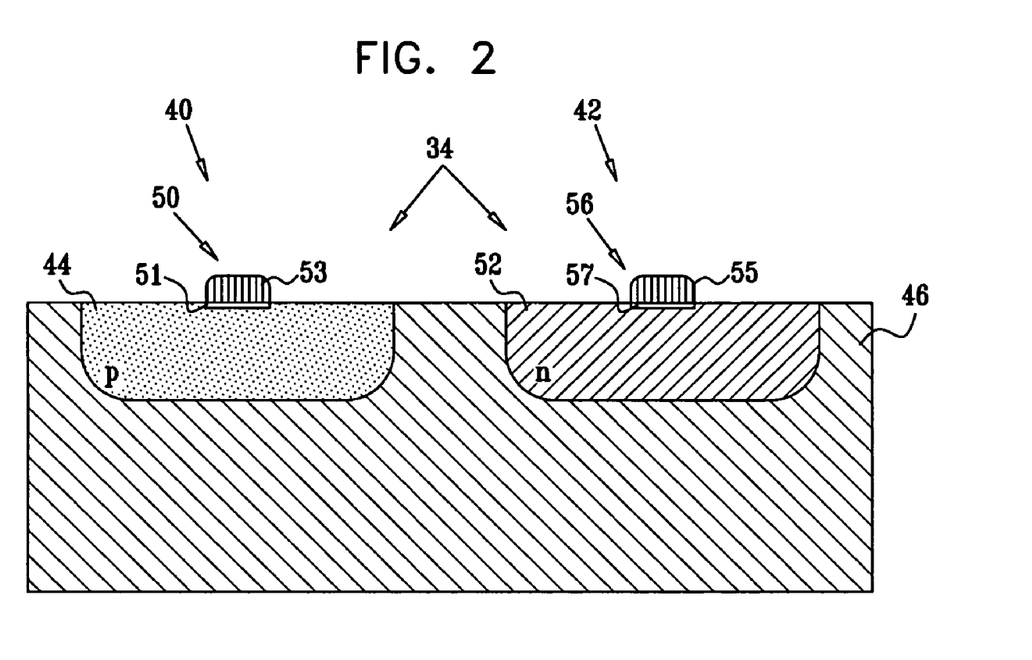
FIG. 2 shows schematic cross-section views of two transistors in a state immediately after a poly-silicon etch stage, according to an embodiment of the present invention.

FIG. 2 shows schematic cross-section views of two transistors 34 in states immediately after a poly-silicon etch stage, according to an embodiment of the present invention. The states illustrated are prior to implantation of sources and drains into the transistors. A first transistor 40 is an N-type MOS transistor and a second transistor 42 is a P-type MOS transistor. Transistor 40 is formed by a p-doped well 44 in a substrate layer 46. A gate 50 comprises a semi-conducting poly-silicon or conducting metal layer 53 formed over a gate oxide dielectric layer 51 on the surface of well 44. Transistor 42 is formed by an n-doped well 52 in substrate 46. A gate 56 comprises a semi-conducting poly-silicon or conducting metal layer 55 formed over a gate oxide dielectric layer 57 on the surface of well 52. Gates 50 and 56 are typically formed at the conclusion of the poly-silicon etch stage, and typically have lateral dimensions of the order of 50–500 nm. While the following description relates to measurements on transistors 40 and 42 immediately after the poly-silicon etch stage, when the gates of the transistors are exposed, it will be appreciated that the principles of the present invention apply to transistors in other stages of fabrication, such as after a stage where conductors have been formed on gates 50 and 56. Thus, those skilled in the art will be able to use the following description, mutatis mutandis, to apply to other stages of the fabrication process.

Figure 3:
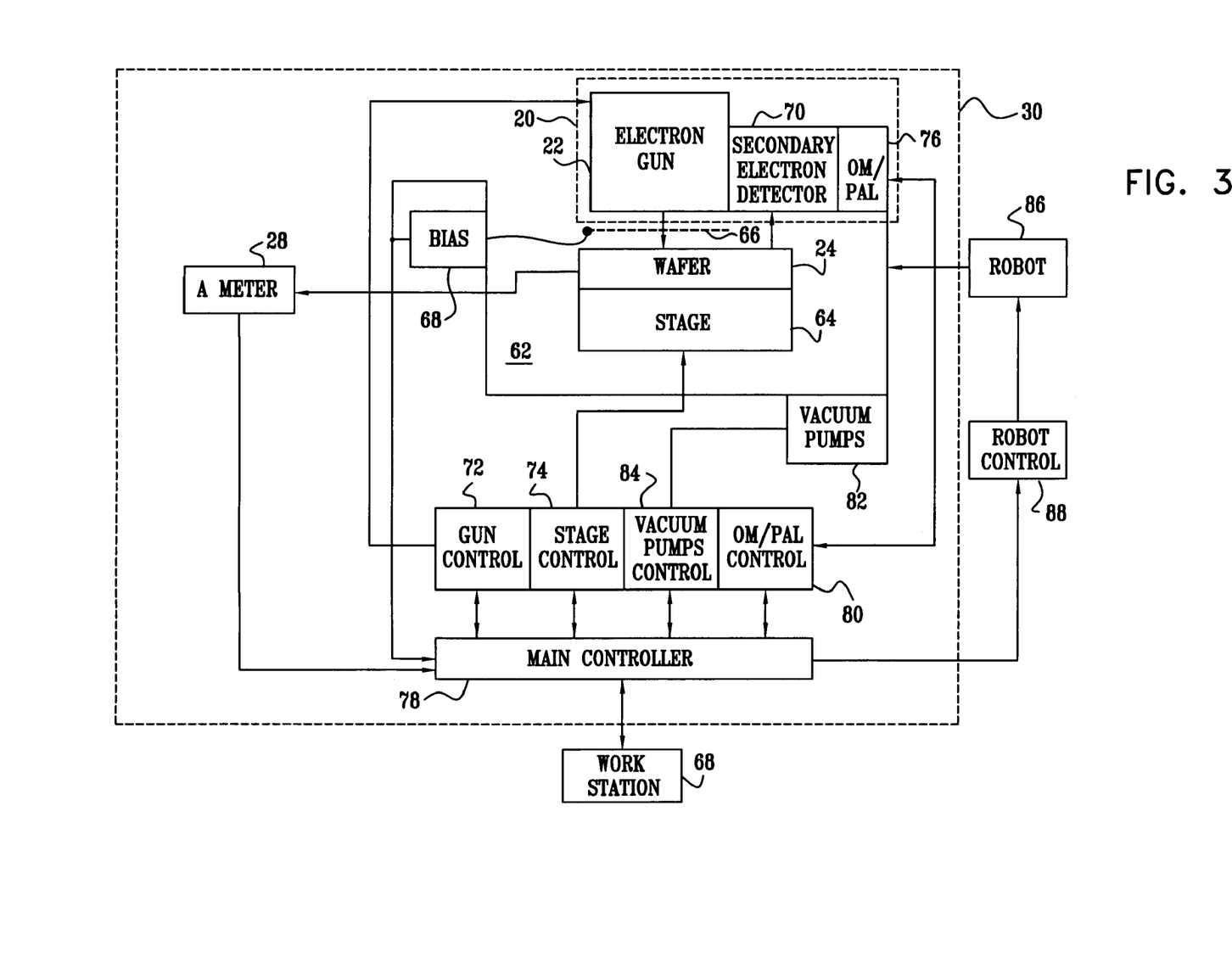
FIG. 3 is a block diagram that schematically illustrates a gate leakage measurement test station, according to an embodiment of the present invention.

FIG. 3 is a block diagram that schematically illustrates gate leakage measurement test station 30, according to an embodiment of the present invention. Station 30 comprises SEM 20, and the SEM and the station are operated by a main controller 78. Station 30 further comprises a chamber 62, containing a motion stage 64 on which wafer 24 is placed during gate leakage measurement, or during a process learning stage typically performed prior to the leakage measurement. As stated above, SEM 20 comprises charged particle generator 22, herein assumed to be an electron gun.

Controller 78 operates the gun, including controlling the energy, the flux, and the dimensions of beam 26, as well as controlling the location on wafer 24 which the beam irradiates, by using a gun control unit 72 and a stage control unit 74. In station 30, controller 78 adjusts the beam diameter and the position of the wafer so that the beam substantially only irradiates a gate under investigation. Thus, the beam typically irradiates a field of view in the range 50–500 nm, so that the irradiation area is within the gate structure being evaluated. Controller 78 also varies the electron energy of the gun, typically between about 100 and 5000 eV, so as to cover both positive and negative charging domains of the gates in the wafer being irradiated. (Positive and negative charging domains are described in the Background of the Invention.) Any commercially available electron beam gun providing the specifications above may be used for the gate leakage station. Alternatively, other types of particle beam generators may be used in station 30.

Typically, a pre-alignment unit based on a low-resolution optical microscope (OM/PAL) 76 is used by controller 78, via an OM/PAL control unit 80, to locate a specific gate, or a test area described in more detail below, on the wafer. During operation, a vacuum is maintained in chamber 62 by a vacuum pump 82, which is also controlled and monitored by controller 78, via a vacuum control unit 84. A robot 86 inserts wafers into chamber 62 and removes them from the chamber. Controller 78 communicates with the robot via a robot control unit 88. Robot 86 may be used to transfer wafers to and from other stations in a cluster tool.

SEM 20 comprises a secondary electron detector 70, which receives secondary, backscattered, and/or Auger electrons caused by electron beam 26 impinging on wafer 24. In the specification and in the claims, secondary, backscattered, and/or Auger electrons are also termed reflected electrons. Detector 70 typically collects the reflected electrons with a high efficiency, of the order of 90% or more. Such a high efficiency can be achieved, for example, using a magnetic immersion lens, which forms a magnetic bottle at the surface of the wafer. Lenses of this sort are described in U.S. Pat. Nos. 4,864,228 and 4,912,405, which disclosures are incorporated herein by reference.

The primary beam current $I_p$ and the secondary detector current are both measured by controller 78. Measurement of the secondary detector current enables a precise location of the gate structure being evaluated to be made.

In a disclosed embodiment of the present invention, detector 70 is configured to act as an energy spectral analyzer for the reflected electrons. The analysis is typically performed in conjunction with controller 78. Energy spectral analyzers are known in the art, and an example of an Auger electron analyzer is described in U.S. Pat. No. 6,781,126, whose disclosure is assigned to the assignee of the present invention, and which is incorporated herein by reference.

Ammeter 28 measures current $I_w$ flowing between the wafer and ground. The ammeter is typically electrically coupled to the lower side of wafer 24, in electrical contact with substrate layer 46. Alternatively, the ammeter may be coupled directly to an intermediate semiconductor or conductive layer in the wafer, assuming that the layers on wafer 24 are suitably configured to enable such coupling. In one embodiment, wafer 24 may include one or more conductive contact pads (not shown in the figures) formed on the underside of the wafer, for use in coupling ammeter 28 to the substrate or intermediate layer.

In an alternative embodiment of the present invention, a bias electrode 66, which may be positively or negatively biased by a biasing power supply 68, may be used to vary a voltage at the surface of the wafer. This application of the bias electrode is described below in more detail with reference to FIGS. 4 and 5. Electrode 66 is physically separate from wafer 24. A description of a suitable electrode and power supply is given in U.S. Patent Application Publication 2004/0021076, which is assigned to the assignee of the present invention and which is incorporated herein by reference.

Stage 64 positions wafer 24 so that in investigating transistors 40 and 42, each of gates 50, 56 is properly located in turn in beam 26. For simplicity and economy of space, stage 64 may comprise an R-theta (translation/rotation) stage. Alternatively or additionally, any other type of motion system with sufficient accuracy may be used for this purpose. For example, the stage may provide X-Y translation, or generator 22 may be translated over wafer 24, or the charged beam itself may be deflected.

After positioning stage 64, controller 78 fires generator 22 to irradiate each of gates 50 and 56 in a controlled manner, described below, and receives current $I_w$ measured by ammeter 48, and current $I_p$. It uses the measured currents to evaluate the leakage current for the gates, according to benchmarks that have been established for the expected gate size and construction. Methods for determining these benchmarks are described hereinbelow with reference to the figures that follow. If the controller determines that the measured current is outside a predetermined tolerance range of a given benchmark, it typically interrupts the production process and notifies a system operator via a user workstation 88. The operator evaluates the test results and then implements whatever corrective action may be necessary.

Figure 4:
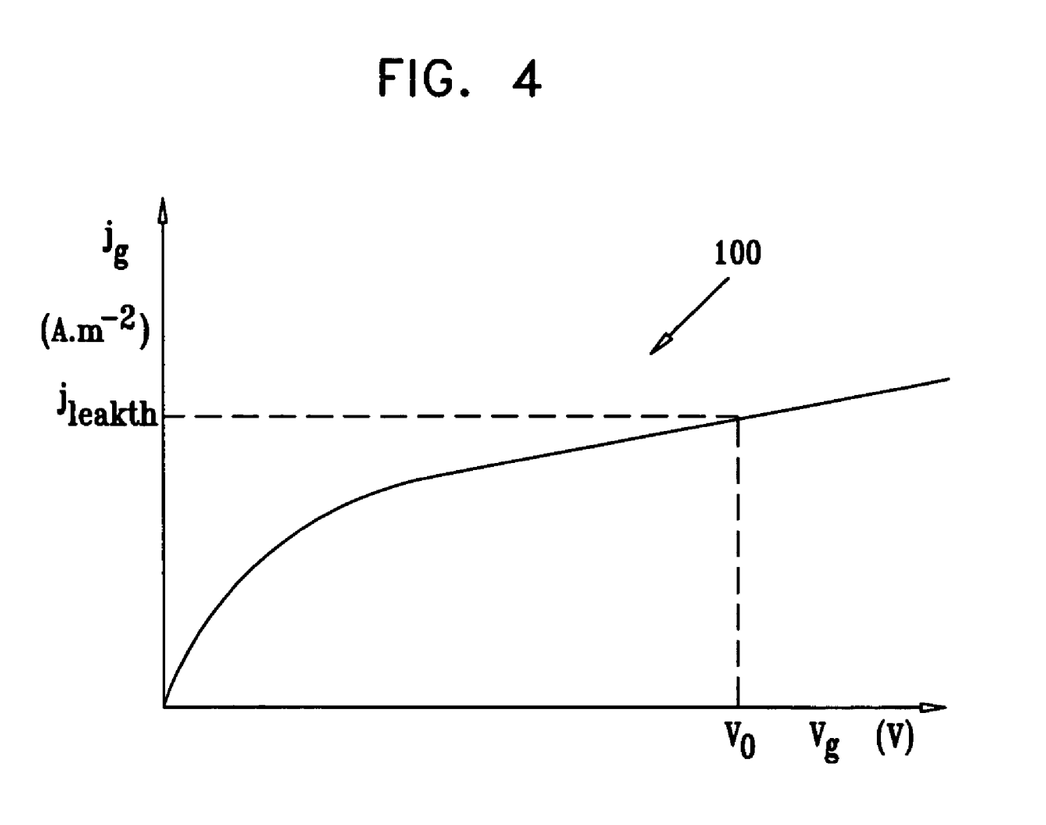
FIG. 4 is a schematic graph of gate leakage current density vs. gate voltage, according to an embodiment of the present invention.

FIG. 4 is a schematic graph 100 of gate leakage current density ($j_g$) vs. gate voltage ($V_g$), according to an embodiment of the present invention. A graph such as graph 100 is typically generated by conventional electrical test equipment in a process learning phase for each process/product within a fabrication facility. Thus, a first $j_g$ vs. $V_g$ graph corresponding to the gate structure of gate 50, and a second $j_g$ vs. $V_g$ graph corresponding to the gate structure of gate 56, are prepared in the learning phase, typically prior to using apparatus 20 for gate leakage measurements. The graphs are generated by measuring gate structure test patterns, the patterns comprising gates similar in construction to the production gates being tested. The gate structure test patterns have known areas and dielectric layer thicknesses, and enable an operator of apparatus 20 to determine the benchmarks referred to above.

To measure the leakage, the patterns may be irradiated by generator 22, the generator being configured to provide positive charging to the gate test pattern being measured. Positive charging, corresponding to a secondary electron yield δ>1, is implemented by adjusting the electron beam energy. A steady-state voltage on the gate test pattern, $V_g$, is varied by changing the bias applied by bias control 68 to electrode 66. Biasing the electrode positively increases the steady-state voltage on the gate; setting the electrode to have a slight negative voltage decreases the gate steady-state voltage. The gate leakage current of the test pattern at steady-state is equal to a saturation current value $I_{wsat}$, described in more detail with reference to FIG. 5 below.

In the case that detector 70 is implemented as an electron energy spectral analyzer, controller 78 determines the steady-state voltage to a resolution down to 0.1 V using a reflected electron distribution, and/or one or more Auger peak shifts, provided by the analyzer. Both methods are known in the art. For example, the book "Methods of surface analysis: Technique and Applications", edited by J. M. Walls (Cambridge University Press, 1989) describes analysis using Auger peaks. Articles "VLSI testing using the electron probe", Scanning electron microscopy, p. 285 (1979) by H. P. Feuerbaum, and "Fundamentals of electron beam testing of integrated circuits", by E. Menzel and E. Kubalek, Scanning, vol. 5, 3, p. 103 (1983) describe electron energy spectrometry.

Figure 5:
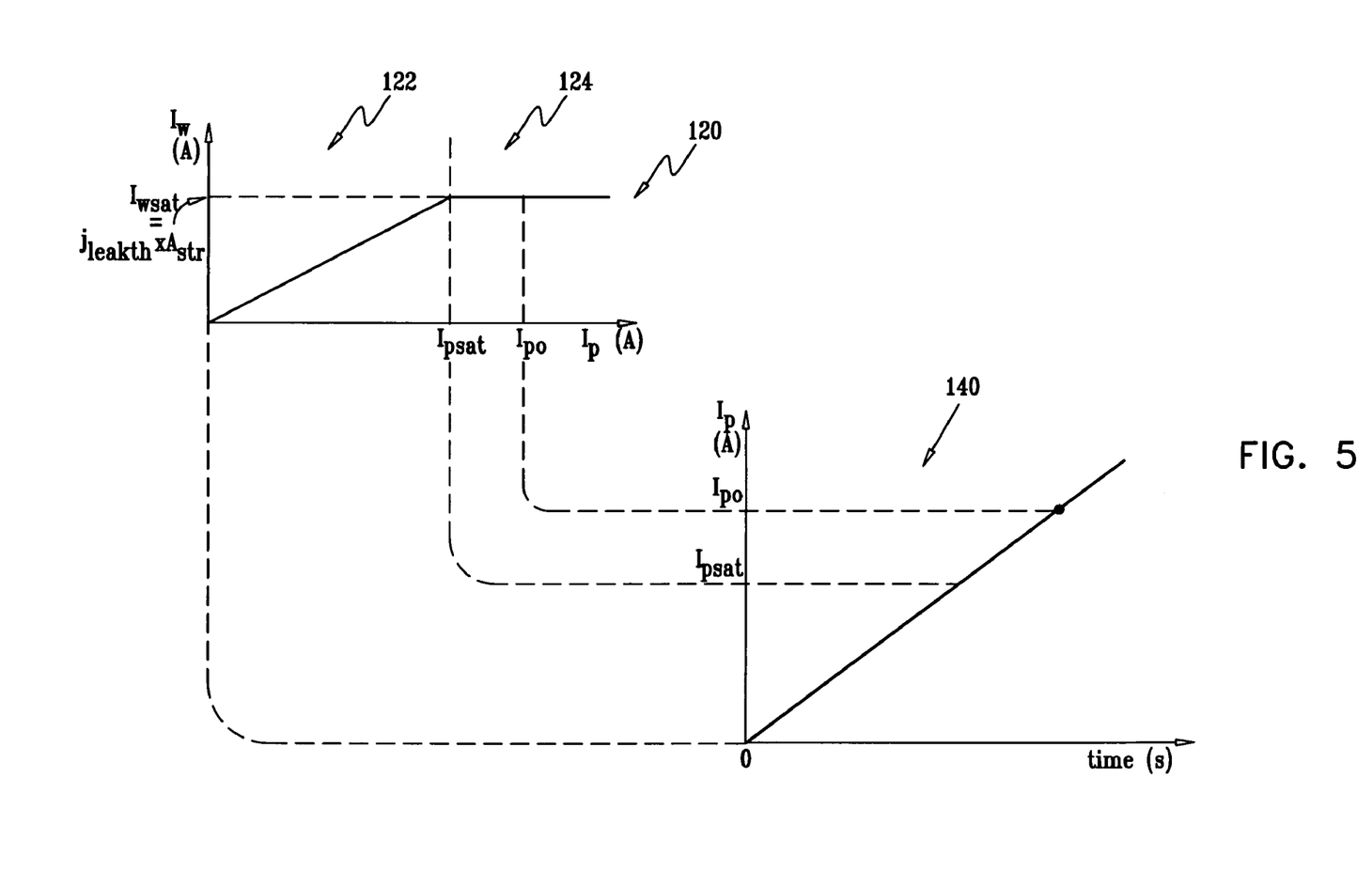
FIG. 5 shows a schematic graph of wafer current vs. primary charge beam current, and a related schematic graph of primary charge beam current vs. time, according to an embodiment of the present invention.

FIG. 5 illustrates a schematic graph 120 of wafer current $I_w$ vs. primary charge beam current $I_p$, and a related schematic graph 140 of $I_p$ vs. time t, according to an embodiment of the present invention. Graphs 120 and 140 are typically generated on real in-die gate structures in the process learning phase mentioned above.

Graph 120 shows a relation between the wafer current and the primary charge beam current, for a gate having the same leakage characteristic as the test pattern described above with reference to FIG. 4. Graph 120 has two regions, a region 122 of values of $I_p < I_{psat}$, and a region 124 of values of $I_p > I_{psat}$. $I_{psat}$ is a boundary value of $I_p$, and is the minimum beam current required to obtain wafer current saturation.

In region 122, where $I_p < I_{psat}$, and assuming $\delta > 1$, then the gate will not charge because all charge on the gate dissipates. In this region the wafer current $I_w$ is given by:

$$I_w = (\delta - 1) \cdot I_p \quad (1)$$

As is illustrated by graph 120, in region 122 wafer current $I_w$ increases in a generally monotonic fashion as $I_p$ increases, up to a saturated wafer current $I_{wsat}$.

In a region 124 of the graph where $I_p > I_{psat}$, the gate will charge to its steady state working potential, since the primary beam current exceeds the gate leakage current. The fully charged gate will cause saturation in the wafer current $I_{wsat}$, as shown in the graph, at $I_p > I_{psat}$, so that the relation of equation (1) no longer holds. The fully charged gate causes the value of $\delta$ to become 1. As illustrated in graph 120, $I_{wsat}$ occurs at primary beam currents $I_p > I_{psat}$. In contrast to region 122, in region 124 $I_w$ is substantially constant with increasing $I_p$.

An expression for $I_{wsat}$ is given by:

$$I_{wsat} = j_{leakth} \cdot A_{str} \quad (2)$$

where $j_{leakth}$ is the current leakage threshold density of the gate (see FIG. 4), and $A_{str}$ is the area of the real in-die gate structure.

Referring back to FIG. 3 and FIG. 4, the gate leakage current threshold density, $j_{leakth}$, for a specific $V_0$, may be determined using electrode 66 to set $V_g$. Typically $V_0$ is set to be in a range from 3V–5V, and $j_{leakth}$ for the specific $V_0$ (see FIG. 4) acts as a benchmark for gate structures to be tested in a production phase at $V_0$ (see FIG. 5).

In such a production phase, wherein a leakage current of a gate is checked, it is advantageous to irradiate the gate with an operating primary beam current $I_{po}$ that is in region 124, i.e., that is greater than $I_{psat}$. A value of $I_{po}$ to be used may be determined using a procedure illustrated by graph 140. In graph 140 the primary beam current $I_p$ irradiating the gate test structure is ramped over a time t, typically in the process learning phase described above, and typically at a fixed bias value on bias electrode 66. As $I_p$ increases, the value of $I_w$ is noted, and a value of $I_{po} > I_{psat}$, where $I_w$ saturates, is selected as the operating primary beam current for testing the gate.

Typical current values to be used in generating graphs such as graph 140 may be determined from values of the gate dimensions and currents, such as the gate parameters given by Stathis, in the article referred to in the Background of the Invention. Using values given in the article, for a gate thickness of 1.5 nm and an area of $5 \cdot 10^{-10}$ cm$^2$, a nominal threshold gate leakage current is approximately 5 nA. In this case, $I_p$ is typically set to be in a range from 0 nA to approximately 10 nA.

Once the value for $I_{po}$ to be used is determined, it is used in the production phase, and values of $I_w$ generated by a gate being checked are compared with the expected value of $I_{wsat}$ for the gate. The comparison determines if a gate is within specification.

It will be appreciated that the measurements of $I_{wsat}$, as described above, enable easy measurements of gate leakage currents to be made at any required gate voltage, and that the measurements may be made on production gates in an in-line process. Gates may be checked in station 30 in a substantially automatic manner, to verify if the gates are within specification, i.e., if expression (3) is true.

$$\frac{I_{wsat}}{A_{str}} \leq j_{leakth} \quad (3)$$

Alternatively, if a gate is found to be outside specification, i.e., if expression (4) is true, the automatic checking may be configured to warn the operator of test station 30.

$$\frac{I_{wsat}}{A_{str}} > j_{leakth} \quad (4)$$

It will further be appreciated that the embodiments described hereinabove for measuring gate leakage do not rely on using electrical contacts to the gates, or test structures having the same structure as the gates, such as are used by prior art systems. Such prior art systems are typically time consuming and destructive, in contrast to embodiments of the present invention, which are quick and non-destructive to implement, and which also may be incorporated into the fabrication process.

Figure 6:
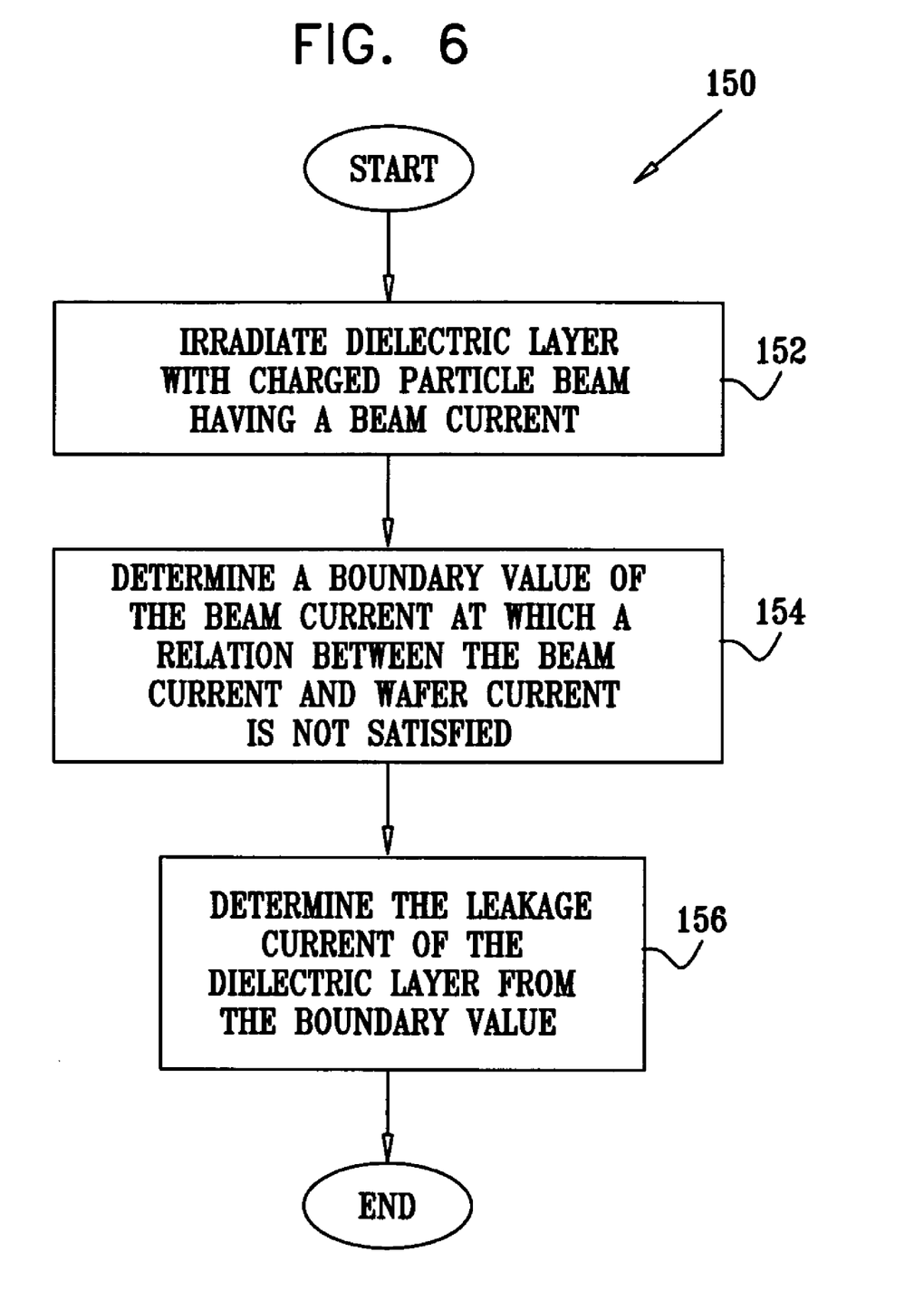
FIG. 6 is a flowchart showing steps involved in using the apparatus of FIG. 1 to measure leakage through a dielectric layer, according to an embodiment of the present invention.

FIG. 6 is a flowchart 150 showing steps involved in using apparatus 20 to measure leakage through a dielectric layer, according to an embodiment of the present invention. In a first step 152, the dielectric layer, such as layer 51 (FIG. 2) is irradiated with a charged particle beam. As described above with reference to FIGS. 3–5, the beam has a beam current $I_p$ which generates a wafer current $I_w$ having a relation to the beam current in a selected range of the beam current, corresponding to region 122 (FIG. 5).

In a second step 154, a boundary value of the beam current is determined, the boundary value corresponding to the beam current at which the relation is not satisfied. Referring back to FIG. 5, the boundary value is the beam current $I_{psat}$.

In a final step 156, the leakage current through the dielectric layer is determined from the boundary value. As described with reference to FIG. 5, the leakage current is $I_{wsat}$.

While the description above has generally considered electrons as the charged particle beams, it will be appreciated that other charged beams, such as positively charged ions, may be used to determine a gate leakage current. All such charged particle beams are to be considered as being within the scope of the present invention.

It will also be understood that while the description above refers generally to gates of transistors, the scope of the present invention may be equally applied to measuring leakage of dielectric layers in structures other than gates. Such structures include, but are not limited to, dielectric layers used in forming capacitors, such as the capacitors used in dynamic random access memory (DRAM).

It will thus be appreciated that the embodiments described above are cited by way of example, and that the present invention is not limited to what has been particularly shown and described hereinabove. Rather, the scope of the present invention includes both combinations and subcombinations of the various features described hereinabove, as well as variations and modifications thereof which would occur to persons skilled in the art upon reading the foregoing description and which are not disclosed in the prior art.

We claim:

1. A method comprising:
irradiating a dielectric layer of a semiconductor device on a wafer with a charged particle beam having a beam current, so as to generate a wafer current between the wafer and ground, the beam current having a value equal to or greater than a saturation beam current established by determining, for a test structure, a boundary value of the beam current at which the wafer current saturates;
measuring the wafer current; and
determining whether the dielectric layer meets a benchmark associated with a leakage current at the boundary value of the beam current by comparing the wafer current so measured to a wafer current saturation value associated with the test structure.

2. The method according to claim 1, wherein the charged particle beam comprises an electron beam.

3. The method according to claim 1, wherein the test structure has a construction substantially similar to that of a structure comprising the dielectric layer and having a known dielectric layer area and thickness.

4. The method according to claim 1, further comprising setting a voltage of a structure comprising the dielectric layer to a preset value, and measuring the wafer current at the preset value.

5. The method according to claim 4, wherein setting the voltage of the structure to the preset value comprises applying the voltage by means of a bias electrode physically separated from the wafer.

6. The method according to claim 5, and comprising determining a current density versus voltage characteristic of the dielectric layer by means of the bias electrode.

7. The method according to claim 4, wherein setting the voltage comprises determining the voltage by spectral analysis of reflected electrons from the wafer.

8. The method according to claim 1, wherein the dielectric layer is formed within a gate comprised in the semiconductor device, and wherein irradiating the dielectric layer comprises irradiating the gate.

9. The method according to claim 8, wherein the gate comprises at least one of a conductor and a semi-conducting layer coupled to the dielectric layer, and wherein irradiating the gate comprises irradiating at least one of the conductor and the semi-conducting layer.

10. The method according to claim 1, wherein the dielectric layer is formed within a capacitor comprised in the semiconductor device, and wherein irradiating the dielectric layer comprises irradiating the capacitor.

* * * * *